(12) United States Patent
Subbian et al.

(10) Patent No.: US 10,883,121 B2
(45) Date of Patent: Jan. 5, 2021

(54) PROCESSES FOR FERMENTATION AND PURIFICATION OF VALUE ADDED PRODUCTS FROM GASEOUS SUBSTRATES

(71) Applicant: STRING BIO PRIVATE LIMITED, Bangalore (IN)

(72) Inventors: Ezhil Subbian, Bangalore (IN); Karthikeyan Thillai, Villupuram (IN); Divakar Duraiswami, Salem (IN); Vinod Munisanjeeviah Lakshmi Devi Kumar, Bangalore (IN); Naga Sairam, Bangalore (IN); Purvesh Girdharbhai Shingala, Bangalore (IN); Sandeep Kumar Chavana, Hyderabad (IN)

(73) Assignee: STRING BIO PRIVATE LIMITED, Bangalore (IN)

( * ) Notice: Subject to any disclaimer, the term of this patent is extended or adjusted under 35 U.S.C. 154(b) by 22 days.

(21) Appl. No.: 16/098,511

(22) PCT Filed: May 9, 2017

(86) PCT No.: PCT/IB2017/052688
§ 371 (c)(1),
(2) Date: Nov. 2, 2018

(87) PCT Pub. No.: WO2017/195103
PCT Pub. Date: Nov. 16, 2017

(65) Prior Publication Data
US 2019/0144890 A1 May 16, 2019

(30) Foreign Application Priority Data

May 9, 2016 (IN) .......................... 6038/CHE/2015

(51) Int. Cl.
| | |
|---|---|
| *C12P 1/04* | (2006.01) |
| *C12P 7/46* | (2006.01) |
| *C12P 7/54* | (2006.01) |
| *C12P 7/56* | (2006.01) |
| *B01F 3/04* | (2006.01) |
| *C12M 1/00* | (2006.01) |

(52) U.S. Cl.
CPC ............ *C12P 1/04* (2013.01); *B01F 3/04106* (2013.01); *C12M 29/06* (2013.01); *C12P 7/46* (2013.01); *C12P 7/54* (2013.01); *C12P 7/56* (2013.01); *B01F 2003/0439* (2013.01); *Y02E 50/10* (2013.01); *Y02E 50/30* (2013.01); *Y02P 20/582* (2015.11)

(58) Field of Classification Search
None
See application file for complete search history.

(56) References Cited

U.S. PATENT DOCUMENTS

| | | | |
|---|---|---|---|
| 5,593,886 A | 1/1997 | Gaddy | |
| 8,178,330 B2 | 5/2012 | Trevethick et al. | |
| 2014/0212937 A1* | 7/2014 | Li | ....................... B01F 3/04751 435/139 |
| 2015/0111265 A1* | 4/2015 | Lidstrom | .............. C12P 7/6463 435/134 |

FOREIGN PATENT DOCUMENTS

EP  0909328 A4  11/1999

OTHER PUBLICATIONS

Balan, "Current Challenges in Commercially Producing Biofuels from Lignocellulosic Biomass", ISRN Biotechnology, vol. 2014, Article ID 463074, pp. 1-31. (Year: 2014).*
Aug. 8, 2017—PCT/IB2017/052688—ISR & WO.
1992—Murrell, J., "Genetics and molecular biology of methanotrophs," FEMS Microbiology Letters, vol. 88, No. 3-4, pp. 233-248.
1996—Hanson, R. S., & Hanson, T. E., "Methanotrophic Bacteria," Microbiological Reviews, vol. 60, No. 2, pp. 439-471.
2014—Qiang Fei et al., "Bioconversion of natural gas to liquid fuel: Opportunities and challenges," Biotechnology Advances,vol. 32, No. 3, pp. 596-6.
Oct. 18, 2018—PCT/IB2017/052688—IPRP.

* cited by examiner

*Primary Examiner* — Michelle F. Paguio Frising
(74) *Attorney, Agent, or Firm* — Banner & Witcoff, Ltd.

(57) ABSTRACT

The present disclosure is related to a process comprising steps of fermentation, separation and purification that can be carried out in a centralized facility with large scale fermentation or in a decentralized facility with smaller scales of fermentation to make value added products from substrate not limiting to gaseous substrates effectively. The fermentation involves fermentative production of a marketable product using reactors or fermentors which are optimized for influential parameters such as gaseous substrate, gas hold up, mass transfer coefficient, etc. The separation step involves an effective way of separating desired product from fermentation broth by employing filtration, precipitation or adsorption techniques thereby enabling easy transportation of the product in case of a decentralized facility. The final stage of the process, either in centralized or decentralized facility, includes the elution of retained product and further purification of the same using downstream processing techniques.

14 Claims, 5 Drawing Sheets

PROCESSES FOR FERMENTATION AND PURIFICATION OF VALUE ADDED PRODUCTS FROM GASEOUS SUBSTRATES

CROSS-REFERENCE TO RELATED APPLICATIONS

This application is a U.S. National Stage application under 35 U.S.C. § 371 of International Application PCT/IB2017/052688 (published as WO 2017/195103 A1), filed May 9, 2017, which claims the benefit of priority to Indian Application 6038/CHE/2015, filed May 9, 2016. Benefit of the filing date of each of these prior applications is hereby claimed. Each of these prior applications is hereby incorporated by reference in its entirety.

TECHNICAL FIELD

The present disclosure in general relates to the field of industrial biotechnology and more specifically pertains to processing and production of value added products by employing fermentation technology. The present disclosure particularly relates to a process comprising steps of fermentation, separation and purification for producing value added products from substrates, not limiting to gaseous substrates, wherein said process is carried out in a centralized facility with large scale fermentation or in a decentralized facility with smaller scales of fermentation. Preferably, the present disclosure relates to a process of gaseous fermentation that significantly enhances the efficiency of gas conversion.

BACKGROUND OF THE DISCLOSURE

Methane is a potent greenhouse gas as well as an abundant energy source. Worldwide estimates of methane from natural gas is 194 trillion $m^3$ which can provide ten times the worldwide energy consumption for 2020. Biogas produced from anaerobic digestion of organic waste is another abundant source of methane. Biogas is mostly a mixture of methane (55-65%) and carbon dioxide (45-35%).

To date, Fischer-Tropsch's process for methane or thermochemical conversion is the only commercial process available to convert methane into a usable form. The Fischer-Tropsch's process involves a series of chemical reactions that produce a variety of hydrocarbons, ideally having the formula $(C_nH_{(2n+2)})$. The more useful reactions produce alkanes as follows:

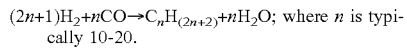

$(2n+1)H_2 + nCO \rightarrow C_nH_{(2n+2)} + nH_2O$; where $n$ is typically 10-20.

Most of the alkanes produced tend to be straight-chain, suitable as diesel fuel. In addition to alkane formation, competing reactions give small amounts of alkenes, as well as alcohols and other oxygenated hydrocarbons.

However, Fischer Tropsch's process is limited by high temperature/pressure requirement, high capital requirements and low efficiencies. Fischer Tropsch's process is also economical only at very large scales. Smaller sources of methane are mostly either vented or flared, adding to GHG (Green House Gas) emissions.

Biological conversion of gases such as methane can occur at nominal temperature and pressure and offers advantages such as no catalyst poisoning, low operating costs and higher specificity. However, gas fermentations are particularly limited by the solubility of the gas in the liquid medium. Solubility of the gases is affected by parameters such as pressure, gas/liquid surface area, concentration gradient, temperature etc. Also, gas fermentation are inherently more challenging due to the tri-phasic nature of fermentation. The instant disclosure intends to overcome such drawbacks in fermentation processes.

With regards to scalability of fermentative processes, value added products produced fermentatively from renewable substrates such as waste, sugarcane, corn, lignocellulose etc., have gained huge importance in recent years. Commercial production of value added products like ethanol, isobutanol, n-butanol, lactic acid, succinic acid, adipic acid happen at >100-500 $M^3$ scale. Often the vertically scaled processes have long development lifecycles and have issues at scale. For example, issues of poor process control, lower performance, contamination etc. The high cost and availability of raw material is another limitation of this process. The present disclosure intends to overcome such limitations.

Existing technologies for production of bio-based products work economically only with very high volume of fermentation processes, particularly for commodity products. However, scaling up from pilot to commercial volumes has proven to be particularly difficult for various fermentative products. While it is relatively easy to control process parameters at smaller scales of fermentation, it is very difficult to control these effectively at very large volumes. Scale up has been limited by contamination, sub-par performance at scale etc. Hence, the present disclosure intends to overcome such limitations in scaling-up.

Methanotrophs or methanotrophic bacteria are unique in their ability to utilize methane as a sole carbon and energy source. However, the methanotrophs are not well established industrial hosts. They are present in a wide variety of environments and play a critical role in the oxidation of methane in the natural world (Hanson, R. S., & Hanson, T. E. (1996). Methanotrophic bacteria. *Microbiological Reviews*, 60(2), 439-471). The methanotrophs are classified into two major groups based on the pathways used for assimilation of formaldehyde, the major source of cell carbon, and other physiological and morphological features. Type I methanotrophs employ the RuMP pathway for formaldehyde assimilation, whereas type II methanotrophs employ the serine pathway for formaldehyde assimilation. The use of enzymes known as methane monooxygenases—MMOs (EC 1.14.13.25) to catalyze the oxidation of methane to methanol is a defining characteristic of methanotrophs. The oxidation of methane by aerobic methanotrophs is initiated by MMOs utilizing two reducing equivalents to split the O—O bonds of dioxygen. One of the oxygen atoms is reduced to form $H_2O$, and the other is incorporated into methane to form $CH_3OH$ methanol. Two forms of MMOs have been found in methanotrophic bacteria, a soluble form (sMMO) and a membrane bound form, pMMO. Methanol is oxidized to formaldehyde by methanol dehydrogenase (MDH), an enzyme that is highly expressed in most methanotrophs. The further oxidation of formaldehyde to carbon dioxide via formate provides most of the reducing power required for the oxidation of methane. Multiple enzymes are known that catalyze the oxidation of formaldehyde to formate. The further oxidation of formate to carbon dioxide is catalyzed by an NAD-dependent formate dehydrogenase. Formaldehyde produced from the oxidation of methane and methanol by methanotrophic bacteria is assimilated to form intermediates of the central metabolic routes that are subsequently used for biosynthesis of cell material. The two known pathways used by methanotrophic bacteria for the synthesis of multicarbon compounds from formaldehyde are the serine pathway, in which 2 mol of formaldehyde and 1 mol of carbon dioxide are utilized to form a three-carbon intermediate, and the RuMP cycle for the assimilation of 3 mol of formaldehyde to form a three-carbon intermediate of central metabolism. Despite such features of methanotrophs being well known in the art, as aforementioned, these are not employed as industrial hosts.

The present disclosure, intends to address such gaps and employ said bacterium in combination with a decentralized approach, at an industrial scale and also provide details of a fermentor and a process that is optimized for efficient gas fermentation and production, in order to overcome limitations of costs, contamination, sub-par performance etc., which are related to scaling up as detailed above.

STATEMENT OF THE DISCLOSURE

Accordingly, the present disclosure relates to a method for processing gaseous substrate(s) to obtain value added product(s), said method comprising: fermenting the substrate(s) to obtain the product(s), separating the product(s) obtained after fermentation, and purifying the separated product(s), wherein the fermentation is carried out by employing pre-determined/optimized parameter(s) of gas liquid mass transfer/or gas residence time, gas:air ratio, gas flow rate and air flow rate; and a method for facilitating processing of gaseous substrate(s) to value added product(s), said method comprising: carrying out fermentation of the substrate(s) to obtain the product(s), at a de-centralized facility in proximity to the source of the substrate(s), separating the product(s) obtained after fermentation at the said de-centralized facility or a centralized facility capable of purifying the separated product(s), and purifying the separated product(s) wherein the fermentation is carried out by employing predetermined/optimized gas liquid mass transfer or/gas residence time, gas:air ratio, gas flow rate and air flow rate.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with detailed description below, are incorporated in and form part of the specification, and serve to further illustrate the embodiments and explain various principles and advantages, in accordance with the present disclosure where:

FIG. 1 illustrates a Centralized process/facility (conventionally known/employed in the art), wherein a centralized approach of fermentation, separation and purification process, is carried out for conversion of gaseous substrates to value added products. Different methods can be employed for purification to obtain varying technical grades of the product.

FIG. 2 illustrates a Decentralized process/facility, wherein an end to end process involving a de-centralized approach of fermentation and separation process and a centralized approach of purification process, is carried out for conversion of gaseous substrates to value added products. As per this process, many small fermentor units are set up in different localities close to availability of the substrate. The product obtained is filtered or precipitated and is transported to a centralized facility for downstream processing.

DETAILED DESCRIPTION OF THE DISCLOSURE

Figure 1:
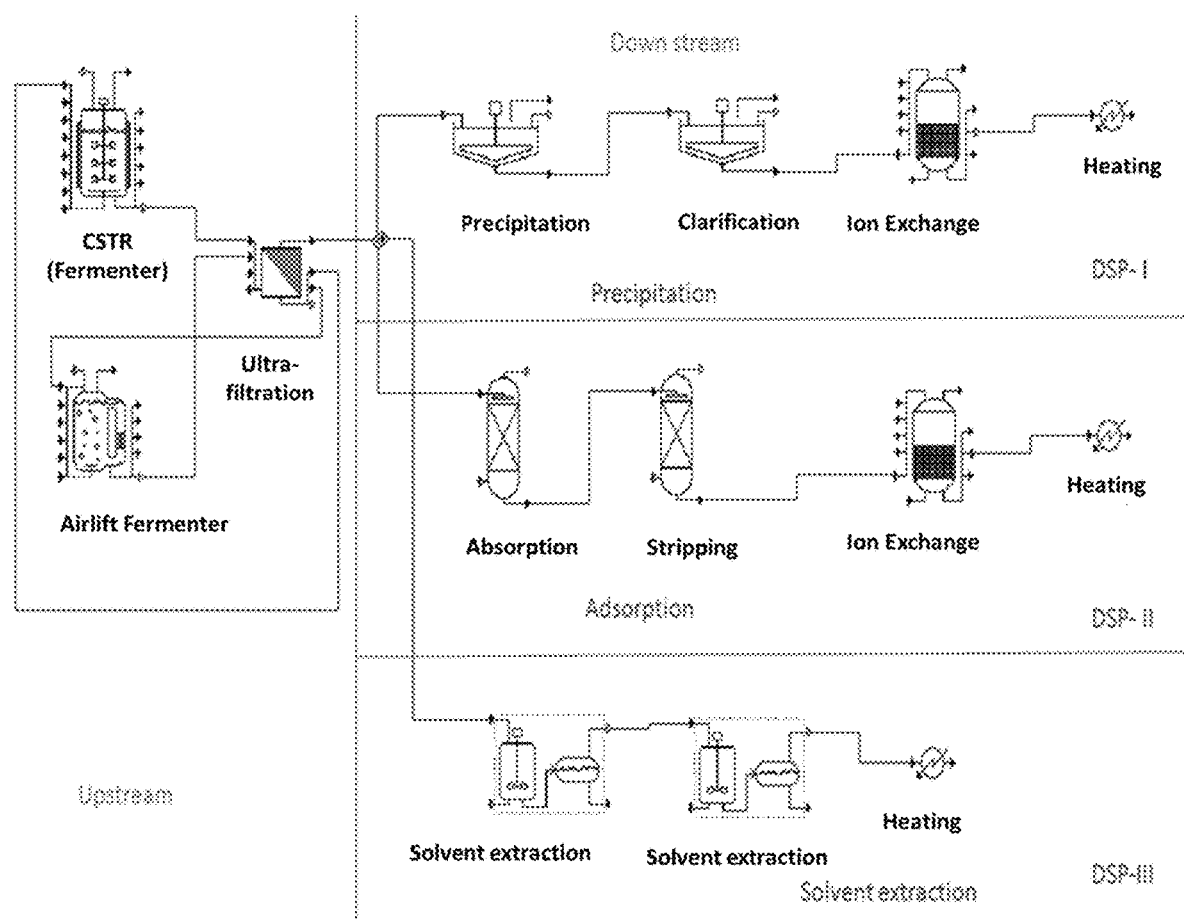

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular as is considered appropriate to the context and/or application. The various singular/plural permutations may be expressly set forth herein for the sake of clarity. Generally, nomenclatures used in connection with, and techniques of industrial biotechnology and fermentation technology described herein are those well-known and commonly used in the art. Certain references and other documents cited herein are expressly incorporated herein by reference. In case of conflict, the present specification, including definitions, will control. The materials, methods, figures and examples are illustrative only and not intended to be limiting.

Furthermore, the process comprising fermentation, separation and purification in a centralized or decentralized facility disclosed employ, unless otherwise indicated, conventional techniques in fermentation technology and related fields. These techniques, their principles, and requirements are explained in the literature and known to a person skilled in the art.

Before the process for producing bio-based value added products from gaseous substrate, the concept of centralized and de-centralized approach and other embodiments of the present disclosure are disclosed and described, it is to be understood that the terminologies used herein are for the purpose of describing particular embodiments only and are not intended to be limiting. It must be noted that, as used in the specification and the appended claims, the singular forms "a," "an" and "the" include plural referents unless the context clearly dictates otherwise.

As used herein, the terms method/process are used interchangeably within this disclosure which relate to the steps employed for obtaining or preparing bio-based value added product(s).

As used herein, the terms "bio-based product(s)" and "value added products(s)" are used interchangeably within this disclosure which relate to the product of the disclosure.

As used herein, the terms "centralized process" or "centralized facility" are used interchangeably within this disclosure and relate to a process or facility wherein the fermentation, product separation and purification are all operated at a single facility or in the same place of operation. The fermentation may be a batch or fed-batch or continuous or other types of fermentation. The separation may be by filtration, membrane separation, centrifugation, precipitation, adsorption or other unit operations to enable product separation. The product purification refers to processing of the product to market/commercial specifications and may be by filtration, precipitation, membrane separation, chromatographic separation, electro-dialysis, solvent extraction, reactive extraction, reverse osmosis, ion-exchange separation, evaporation, drying, distillation or other unit operations to enable purification.

As used herein, the terms "de-centralized process" or "de-centralized facility" or "decentralized process" or "decentralized facility" are used interchangeably within this disclosure and relate to a process or facility wherein the fermentation, product separation and purification are all operated in distributed facilities such that the fermentation is operated in multiple locations usually closer to the sources of substrate and the product separation and purification is in a single centralized location. In some instances, the fermentation and separation could be operated in multiple smaller facilities usually closer to the source of substrate and the product purification could be in a centralized location.

In some instances, the fermentation, product separation and purification resemble a hub and spoke model where the multiple locations of fermentation are connected to a centralized hub for product purification. The product separation could happen at the site of fermentation or the product separation can happen at the site of purification.

As used herein, the terms "in-situ process" and "ex-situ process" are used interchangeably within this disclosure and relate to the process of separation. In some instances, the separation will be "in-situ" or "in place" separation of the products in the fermenter such as by using precipitation. In other instances, the separation will be "Ex-situ" or by extracting the fermentation milieu and processing it separately usually after the fermentation.

As used herein, the term "sparger" within this disclosure, relates to a device or instrument used to sparge or flush gaseous substrate through a liquid. Spargers have thousands of tiny pores that enables the bubbling of gas through the liquid. This increases the gas-liquid contact surface area thereby enhancing the gas transfer.

As used herein, the term "ALF/STR" within this disclosure, relates to types of fermenters used for fermentation of the substrate. "STR" refers to a traditional stirred tank reactor where the mixing is primarily by the rotating stirrer. STRs have been the choice of reactors for most commercial applications. STRs offer excellent mixing, good mass transfer rates and lower cost of production. "ALFs" refers to Air lift fermenters which are pneumatic reactors where the gas/air feed turbulence ensures mixing. The introduction of the gas feed causes a circulatory movement in the reactor. ALFs generally have lower energy requirements at scale.

"Continuous" fermentation refers to the process of fermentation where the products are continuously removed from the fermenter and fresh media or substrate is being added continuously to the fermenter. The exponential growth phase of the microbe is maintained in the reactor for long periods of time. Unlike batch fermentations, the continuous fermentation runs for longer periods of time with addition of nutrients and harvesting of products at steady rates. The rate of addition of nutrients and harvesting of products refers to the "dilution rate" of the continuous fermentation. The dilution rate directly affects the productivity of the overall process.

To overcome the non-limiting drawbacks of the prior art and to provide for a simple, cost-effective and efficient process for producing value added products from substrates, the present disclosure provides a method for carrying out the aforementioned process comprising processing the substrate(s) under suitable conditions to obtain the value-added product(s).

In a non-limiting embodiment, the substrate is preferably a gaseous substrate such as methane, natural gas, syngas, landfill gas, carbon monoxide and/or biogas; but could also be a non-gaseous substrate such as organic waste, kitchen waste, municipal solid waste, agricultural residues, sewage, plant material, green waste, poultry litter, landfill waste and/or similar.

In an alternate embodiment, when the substrate is a non-gaseous substrate, said is converted into bio-gas or methane by well-known conventional techniques and thereafter processed as per the present disclosure to obtain/prepare the value added products.

In an embodiment, the process involves three steps, comprising fermentation of gaseous substrate, separation, and purification to obtain value added products, without the process steps being limited by any specific order and which can be performed in a centralized facility or de-centralized facility or a combination of both, in order to obtain bio-based value added product(s).

The present disclosure particularly relates to a process comprising steps of fermentation, separation and purification for producing bio-based value added products from gaseous substrates effectively, wherein said process can be/is carried out in a centralized facility with a large scale fermentation or in a decentralized facility with smaller scales of fermentation.

In a non-limiting embodiment of the present disclosure, the process involves a fermentation step for producing value added products from gaseous substrates effectively, wherein said step can be/is carried out in a centralized facility employing large scale fermentation or in a decentralized facility employing smaller scales of fermentation or a combination of both.

In a preferred embodiment, the fermentation step is carried out in a decentralized facility.

In another non-limiting embodiment of the present disclosure, the fermentation step involves use of microorganisms in culture/fermentation medium under suitable culture conditions, to convert gaseous substrates to value added products.

In an exemplary embodiment of the present disclosure, the microorganism used may be a wildtype or a recombinant methanotroph.

In another non-limiting embodiment, the methanotroph is selected from a group comprising, but not limiting to *Methylococcus capsulatus, Methylobacterium extorquens, Methylomicrobium album, Methylocapsa acidiphila, Methylobacterium organophilum, Methylobacterium mesophilicum, Methylobacterium dichloromethanicum, Methylocella silvestris, Methylosinus trichosporium, Methylobacillus flagellatus* KT, *Methylibium petroleiphilum* PM1, *Methylobacterium nodulans, Methylobacterium populi, Methylobacterium chloromethanicum, Methylacidiphilum infernorum* V4, *Methylophilus methylotrophus, Methylomonas methanica, Methylobacterium rhodesianum* MB 126, *Methylobacter* tundripaludum, *Methylobacterium* sp. 4-46, *Methylovorus glucosetrophus* SIP3-4, *Mycobacterium smegmatis, Methylobacterium rhodesianum, Methylosinus sporium, Methylocella palustris, Methylobacterium fujisawaense, Methylocystis parvus, Methylovulum miyakonense, Methylobacterium rhodinum, Methylocystis echinoides, Methylomonas rubra, Methylococcus thermophilus, Methylobacterium aminovorans, Methylobacterium thiocyanatum, Methylobacterium zatmanii, Acidithiobacillus ferrivorans, Methylobacterium aquaticum, Methylobacterium suomiense, Methylobacterium adhaesivum, Methylobacterium podarium, Methylobacter whittenburyi, Crenothrix polyspora, Clonothrix fusca, Methylobacter bovis, Methylomonas aurantiaca, Methylomonas fodinarum, Methylobacterium variabile, Methylocystis minimus, Methylobacter vinelandii, Methylobacterium hispanicum, Methylomicrobium* japanense, *Methylococcaceae bacterium*, and *Methylocystis methanolicus*.

In a preferred embodiment of the present disclosure, the methanotroph includes but is not limiting to *Methylococcus*

*capsulatus, Methylosinus trichosporium, Methylocella silvestris, Methylobacterium extorquens.*

In another preferred embodiment of the present disclosure, the methanotroph is *Methylococcus capsulatus*.

In yet another embodiment of the present disclosure, the culture medium/fermentation medium comprises organic and inorganic source of nitrogen optionally along with trace elements.

In a preferred embodiment, the culture medium comprises nitrate mineral salts medium (Murrell, J. (1992). Genetics and molecular biology of methanotrophs. FEMS Microbiology Letters, 88(3-4), 233-248).

In a non-limiting embodiment of the present disclosure, the process involves conversion of gaseous substrates to value added products/bio-based value added product including but not limiting to organic acids.

In another non-limiting embodiment of the present disclosure, the process involves conversion of gaseous substrates to value added products, including but not limiting to single cell protein. Single cell protein is a high protein product made from biomass.

In yet another non-limiting embodiment of the present disclosure, the process involves conversion of gaseous substrates to value added products, including but not limiting to carotenoids.

In still another non-limiting embodiment of the present disclosure, the gaseous substrates include, but are not limiting to methane, biogas, natural gas, syngas, landfill gas and carbon monoxide.

In a non-limiting embodiment of the present disclosure, the organic acid is selected from, but not limiting to a group comprising lactic acid, malic acid, succinic acid, formic acid and acetic acid or any combination thereof. Similarly, carotenoid is selected from a group comprising beta-carotene, lutein, zeaxanthin, lycopene, astaxanthin, annatto or any combination thereof.

In another non-limiting embodiment of the present disclosure, the fermentation is carried out using a fermentor/reactor, not limiting to a stirred tank reactor (STR) or an air lift fermentor (ALF).

In yet another non-limiting embodiment of the present disclosure, the fermentation step employing the fermentor may be operated in batch, fed batch, continuous or semi-continuous mode.

In an exemplary embodiment of the present disclosure, the fermentor used in the process can work as a batch or continuous reactor using gaseous substrate for efficient interaction between the microorganism and the medium, thereby increasing the mass transfer coefficient. The fermentor is designed in a way that it can be scaled up or down depending on the requirement, for example, from ~400 L to ~4,000,000 L capacity or from about ~5000 L to ~1,00,000 L capacity.

In another exemplary embodiment of the present disclosure, for the continuous mode, the dilution rate will be optimal such that overall productivity is the highest.

In another preferred embodiment of the present disclosure, for the continuous mode, the optimal dilution rates of the culture medium is from about 0.03 to about 0.6 per hour; more preferably from about 0.12 to about 0.19 per hour or from about 0.05 to about 0.25 per hour.

In yet another non-limiting embodiment of the present disclosure, the fermentor is optimized for gas hold up, gas recycle, maximum gas residence time, maximum complete gas disengagement and optimal gas conversion.

In a preferred embodiment, optimization of maximum gas residence time/gas liquid mass transfer in-turn affects gas hold up, gas recycle, gas disengagement and gas conversion. The gas hold up refers to the fraction of reactor volume occupied by the gas. The term gas recycle refers to the recycling of residual or partially utilized gas from exhaust back to the fermenter. The term maximum gas residence time refers to the time the gas stays in the fermenter i.e., from the point of entry to exhaust. Maximum complete gas disengagement refers to the separation of gas from the liquid phase post sparging. The term gas conversion refers to the utilization of gas fed to the reactors by the microbes.

In another embodiment, the fermentor and process parameters in the present disclosure are optimized with the objective that the gas conversion rate is at least 1 g/L/h. The gas conversion rate refers to the rate of utilization of the gas that is fed to the reactor. In some instances the gas conversion rate varies from 0.1 to 20 g/L/h. In some instances the gas conversion rate is at least 1 g/l/h.

In another embodiment of the present disclosure, the fermentation step involves maintaining optimal gas-liquid mass transfer. In gas fermentation, the process productivity depends on efficient gas-liquid mass transfer. This in-turn is dependent on gas hold up, gas solubility and gas residence time and is affected by gas flow rate, methane:air ratio, bubble size, agitation etc. Conventional processes have leveraged microbubbles to enhance gas transfer. Microbubbles tend to gradually decrease in size and subsequently collapse due to long stagnation and dissolution of interior gases into the surrounding water. Nanobubbles on the other hand, (<100 nm diameter) have a lower buoyancy and will remain suspended in liquids for an extended period of time. Their use to date has been limited to medical imaging, bioremediation and controlled drug delivery. Nanobubbles offer significant advantages for gas transfer compared to micro or ordinary sized bubbles. Since the size of the bubbles are small, buoyant forces are low and thus nanobubbles do not raise to the surface quickly. Secondly, their surface area to volume ratio is greater which improves gas solubility. Ordinary bubbles grow or shrink by diffusion based on whether the surrounding solution is over or under-saturated with gas relative to the cavities pressure. Since the solubility of gas is proportional to the gas pressure and this pressure is exerted by the surface tension in inverse proportion to the diameter of the bubble, the normal tendency is for bubbles to shrink in size and dissolve in a few microseconds. However, nanobubbles are observed in liquid for days. While the stability of nanobubbles is not well understood, it is thought to be a function of the electric double-layer force of repulsion between bubbles. The significantly higher stability and longevity (days compared to microseconds) of nanobubbles can be a huge advantage for a process dependent on gas transfer such as methane fermentation and hence is employed by the process of the instant disclosure.

In a non-limiting embodiment, gas-liquid mass transfer which is dependent on bubble size in the present disclosure is in nano-scale range. Said nano bubble size is obtained in the instant disclosure by optimizing the sparger pore size in the fermentor/reactor, which is in the range of about 1 mm to about 2 nm. In some instances, the pore size of the sparger ranges from 1 um to about 100 nm. In some instances, the pore size ranges from 500 nm to 100 nm. More preferably, the pore size ranges from about 20 um to about 1 nm.

In still another non-limiting embodiment of the present disclosure, the fermentation step employs optimization of key parameters for fermentor operation.

In still another non-limiting embodiment of the present disclosure, the key parameters for optimization include, but are not limiting to gaseous substrate flow rate (methane or methane and air flow rate), air flow rate, ratio of gaseous substrate (methane) to air, superficial gas velocity, rate of gaseous substrate (methane) recycle, dissolved carbon-dioxide concentration in the media, gas liquid separation, specific growth rate, fermentation temperature, agitation, pressure and pH or any combination of parameters thereof.

In a preferred embodiment, the key process parameters that are optimized include gas residence time, gas transfer coefficient, gaseous substrate flow rate/methane flow rate, air flow rate, ratio of gaseous substrate:air or ratio of methane:air and pressure or any combination of parameters thereof.

In a preferred embodiment of the present disclosure, the gaseous flow rate refers to methane or methane and air combined flow rate that further relates to volume of gas fed to the fermentation medium per unit of time. Optimum gas feed rates vary depending on the size of the fermentor. Workable range for gas flow rate varies from about 0.05 vvm to about 3 vvm. In some instances, it can vary from about 0.1 vvm to about 1 vvm. In some instances, it can be about 2 vvm.

In another exemplary embodiment of the present disclosure, the methane that is fed/introduced into the fermentation medium may not be completely utilized and a percentage of the methane may be pushed out of the reactor unused. Hence, exit stream will have varying amounts of methane that is emitted together with carbon dioxide. The ratios of methane and carbon dioxide in the exit gas stream vary often with higher amounts of carbon dioxide than methane being present. This exit stream is re-cycled into the reactor to further enhance the overall yield of methane conversion. The rate of methane in the recycled stream is optimized for maximum product conversion. In some instances the carbon dioxide in the exit stream from the fermentor is scrubbed and a pure methane stream is recycled into the fermentor. In some instances the exit stream is recycled as is. As methane is being continuously introduced into the medium, the methane is also constantly separated from the liquid and pushed out of the fermentor.

In another non-limiting embodiment of the present disclosure, air flow rate relates to volume of air fed into the fermentation medium per unit of time. Optimum air flow rates vary depending on the size of the fermentor. Workable range for air flow rate varies from about 0.05 vvm to about 3 vvm. In some instances, it can vary from about 0.1 vvm to about 1 vvm. In some instances, it can be around 2 vvm.

In another non-limiting embodiment of the present disclosure, ratio of gaseous substrate (methane) to air relates to ratio of volume of gaseous substrate (methane) to volume of air that is fed to the fermentation medium.

In a preferred embodiment of the present disclosure, optimized methane to air ratios are in the range of about 1:0.1 to about 1:5

In another preferred embodiment of the present disclosure, optimized methane to air ratios are about 1:0.1, about 1:0.2, about 1:0.3, about 1:0.5, about 1:0.6, about 1:0.7, about 1:0.8, about 1:0.9, about 1:1, about 1:1.5, about 1:2, about 1:2.5, about 1:3, about 1:3.5, about 1:4, about 1:4.5, about 1:5.

In another embodiment of the present disclosure, superficial gas velocity relates to volumetric gas flow rate per unit cross sectional area of the fermentor.

In a preferred embodiment of the present disclosure, superficial gas velocity employed, is in the range of about 0.01 m/s to about 0.5 m/s.

In another preferred embodiment, the superficial gas velocity employed, is of about 0.01 m/s, 0.02 m/s, 0.03 m/s, 0/04 m/s, 0.5 m/s.

In still another embodiment, Gas-liquid separation is related to the design of the fermentor which facilitates the media recirculation, gas disengagement, and fraction of gas recirculating in the fermentor.

In still another embodiment, the specific growth rate relates to dilution rate, in case of continuous process. In some instances, the dilution rate of the culture medium varies from about 0.03 h−1 to about 0.6 h−1. In certain instances, the dilution rate varies from about 0.05 h−1 to about 0.25 h−1

In still another embodiment of the present disclosure, the fermentation step is optimized for removal of biomass or product as well as the amount of culture/product being removed.

In still another embodiment of the present disclosure, the fermentation step is carried out at temperature ranging from about 20° C. to about 50° C.

In a preferred embodiment of the present disclosure, the fermentation step is carried out at temperature ranging from about 30° C. to about 45° C.; more preferably at temperature of about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C.

In still another embodiment of the present disclosure, the fermentation step is carried out at pH ranging from about 3.0 to about 8.0.

In a preferred embodiment of the present disclosure, the fermentation step is carried out at pH ranging from about 4 to about 7; more preferably at pH of about 3.5, about 4, about 4.5, about 5, about 5.5, about 5.8, about 6, about 6.5, about 7, about 7.5.

In still another embodiment of the present disclosure, the fermentation step involves agitation of components in the fermentor employed therein, which is maintained at about 200 rpm to about 1000 rpm.

In a preferred embodiment, the agitation is maintained at about 200 rpm, about 210 rpm, about 220 rpm, about 230 rpm, about 240 rpm, about 250 rpm, about 260 rpm, about 270 rpm, about 280 rpm, about 290 rpm, about 300 rpm, about 300 rpm, about 310 rpm, about 320 rpm, about 330 rpm, about 340 rpm, about 350 rpm, about 360 rpm, about 370 rpm, about 380 rpm, about 390 rpm, about 400 rpm, about 410 rpm, about 420 rpm, about 430 rpm, about 440 rpm, about 450 rpm, about 460 rpm, about 470 rpm, about 480 rpm, about 490 rpm, about 500 rpm, about 510 rpm, about 520 rpm, about 530 rpm, about 540 rpm, about 550 rpm, about 560 rpm, about 570 rpm, about 580 rpm, about 590 rpm, about 600 rpm, about 610 rpm, about 620 rpm, about 630 rpm, about 640 rpm, about 650 rpm, about 660 rpm, about 670 rpm, about 680 rpm, about 690 rpm, about 700 rpm, about 710 rpm, about 720 rpm, about 730 rpm, about 740 rpm, about 750 rpm, about 760 rpm, about 770 rpm, about 780 rpm, about 790 rpm, about 800 rpm, about 810 rpm, about 820 rpm, about 830 rpm, about 840 rpm, about 850 rpm, about 860 rpm, about 870 rpm, about 880 rpm, about 890 rpm, about 900 rpm, about 910 rpm, about 920 rpm, about 930 rpm, about 940 rpm, about 950 rpm, about 960 rpm, about 970 rpm, about 980 rpm, about 990 rpm, about 1000 rpm.

In another embodiment of the present disclosure, the fermentation step is carried out at pressure ranging from about 0.5 bar to about 6 bar; preferably at pressure of about 0.5 bar, about 1 bar, about 1.5 bar, about 2 bar, about 2.5 bar, about 3 bar, about 3.5 bar, about 4 bar, about 4.5 bar, about 5 bar, about 5.5 bar, about 6 bar.

In another embodiment of the present disclosure, the process parameters or process influencing parameters such as pH, temperature, agitation, gas flow and other parameters etc as aforementioned are maintained for a time period ranging from about 80 hours to about 100 hours; preferably for about 96 hours. In other instances, the process parameters or process influencing parameters such as pH, temperature, agitation, gas flow and other parameters etc are maintained throughout the fermentation for a continuous process.

In a non-limiting embodiment of the present disclosure, the process involves separation step for producing bio-based value added products from gaseous substrates effectively, wherein said step can be/is carried out in a centralized facility or in a decentralized facility.

In a preferred embodiment of the present disclosure, the separation step involves separation of product obtained after fermentation from fermentation broth, which is carried out using process techniques including, but not limiting to filtration, precipitation or adsorption or a combination of any said techniques. Said separation steps can be carried out in any order of sequence.

In another embodiment of the present disclosure, the separation steps involve separating the product from the fermentation broth by an in-situ process in case of batch fermentation or ex-situ process in case of continuous fermentation, by precipitation, filtration or adsorption. This step of separation provides more flexibility in downstream processing/purification, which cannot be achieved by existing processes in the current field of technology.

In another non-limiting embodiment of the present disclosure, the separation is carried out in a centralized or a de-centralized facility; but preferably is carried out in a de-centralized facility and thereafter transported to a centralized facility for purification.

In a preferred embodiment of the present disclosure, filtration is carried out by employing techniques including but not limiting to ultrafiltration; and precipitation or adsorption which is carried out by employing resins or salts, including but not limiting to ion-exchange resins or calcium salts respectively.

In a non-limiting embodiment, ultrafiltration is carried out by passing culture broth obtained post fermentation though an ultrafiltration unit, to remove cells and other insoluble products from the broth. Process of ultrafiltration can be optimized by varying the applied pressure, flow rate and membrane module used.

In another preferred embodiment of the present disclosure, precipitation is carried out using calcium salts. For example, when the products are organic acids, salts like calcium hydroxide or calcium carbonate are used. The precipitate thus formed, is filtered and directly transported to the centralized downstream processing facility for purification or the precipitate formed is filtered and re-dispersed in water, followed by addition of strong acid(s), not limiting to sulphuric acid and then the precipitate formed therefrom is filtered and then transported to the centralized downstream processing facility for purification, which is the process carried out, post the separation process step.

In a non-limiting embodiment, the pH post addition of calcium hydroxide is maintained in the range of about 9-11, preferably at about 9.5, which enables precipitation. Furthermore, if a two-step precipitation is carried out, as aforementioned, the pH post addition of strong acid, is maintained until pH of about 2.5 to about 3.5 is reached, preferably a pH of about 3 is maintained, which enables precipitation.

In yet another preferred embodiment of the present disclosure, adsorption is carried out using ion-exchange resins. For example, products such as organic acids can also be adsorbed onto ion exchange resins that have high affinity towards the acids.

In still another preferred embodiment of the present disclosure, the ion exchange resins include but are not limited to weak anionic resins with cross linked acrylic or styrene-divinyl benzene copolymeric matrix with a tertiary amine functional group, Eg: amber lite IRA 96 or IR 67; or strong cation exchange resins such as having sulphonic acid funtional groups, Eg: amber lite IR 120

In an exemplary embodiment of the present disclosure, separation step is carried out using continuous, batch or semi-continuous mode.

In a preferred embodiment of the present disclosure, the separation in batch mode involves the resin to be directly added to cell-free fermentation broth at the end of fermentation. Once the resin is saturated, it is removed and transported to the centralized facility for downstream processing and purification.

In another preferred embodiment of the present disclosure, separation in the continuous or semi-continuous mode involves filtrate obtained after cell separation, to be passed through a small column that is easily replaceable. Once the resin is saturated, it is removed and transported to the centralized facility for downstream processing and purification.

In another embodiment of the present disclosure, in a decentralized facility for working the separation and purification process step, the products obtained after fermentation at the onsite facility are separated and thereafter transported to a centralized downstream processing facility for further processing to obtain the purified product. One of the key requirements of this process is the separation and transportation of the crude product efficiently and economically for further purification. The crude product is transported preferably in small volumes. And the purity and quality of the product is maintained during transport, also minimizing contamination concerns.

In yet another embodiment of the present disclosure, in a centralized facility for working the separation and purification step, when the product is for example, an organic acid, calcium salt of the organic acid is suspended in water and to this strong acid such as but not limiting to sulphuric acid, is added. Acidification will precipitate calcium sulfate from the solution which is filtered off. The filtrate is passed through a strong cation exchange resin to remove residual ion and later concentrated using an evaporator.

In still another embodiment of the present disclosure, the resin is filled in a column and a strong base not limiting to NaOH is used to elute the acid and regenerate the resin. The eluted acid is passed through a strong cation exchange resin and later through an evaporator for concentrating and purifying the acid for a desired level.

In a non-limiting embodiment of the present disclosure, the process involves purification step for producing bio-based value added products from gaseous substrates effectively, wherein said step is carried out preferably in a centralized facility.

In a preferred embodiment of the present disclosure, precipitate obtained after the separation step is transported to the centralized facility for purification.

In another preferred embodiment of the present disclosure, the purification or downstream purification including downstream processing is carried out by techniques including but not limiting to electro-dialysis, solvent extraction, reactive extraction, reverse osmosis, filtration, precipitation, membrane separation, chromatographic separation, drying, distillation, ion-exchange and/or evaporation depending upon the product concentration and purity requirements. Electro Dialysis (ED) is a membrane process, where positive or negative ions are transported through semi permeable membrane, under the influence of an electric potential. The membranes can be cation or anion selective. Solvent extraction is a method of liquid-liquid extraction where the product is removed by using another solvent that is immiscible with the media. Reactive extraction is also a form of liquid-liquid extraction where the product can be removed by using another solvent that is immiscible with the media and where the separation is intensified by a reversible reaction between the product and the extractant. Reverse osmosis a process by which a solvent passes through a porous membrane in the direction opposite to that for natural osmosis when subjected to a hydrostatic pressure greater than the osmotic pressure. Reverse osmosis is regularly used for water treatment. Filtration refers to the process of separating of the product by passing through a membrane usually under conditions of pressure. Precipitation refers to product separation by triggering the formation of a solid form of the product that then separates from the liquid. Membrane separation leverages the pores in a membrane to selectively separate mixtures. The process is affected by the pore size and the concentration gradient. Chromatographic separation refers to the use of liquid or gas chromatography for separation of the product. Ion exchange refers to the use of ion-exchange columns for further product separation or purification. The column can be a negative or positive ion exchange column. Drying, Distillation and Evaporation are standard techniques routinely used to remove moisture from the product and enhance concentration. Each of these separation techniques can be optimized by varying the dependent process parameters.

In a non-limiting embodiment, the solvent extraction technique of purification involves subjecting the obtained product post separation step, to elution using a strong base such as NaOH.

In a non-limiting embodiment, the present disclosure also relates to a decentralized end to end facility for carrying out the process of the instant disclosure for producing bio-based value added products from gaseous substrates effectively.

In a preferred embodiment of the present disclosure, the decentralized facility includes many small fermentors with capacity >400 L that can be connected to a centralized purification facility. The centralized facility is set up for making products of different concentration and purity requirements. This allows for the process to be integrated horizontally.

In another embodiment of the present disclosure, separation post fermentation of the product from the milieu allows for transportation of product from smaller fermentation facilities to a larger centralized facility for downstream purification of the product. It provides more flexibility in operation as the process can be carried out in a centralized or decentralized facility. Further, it also allows for small scale deployment of the process where large amounts of substrate are not available. Therefore, the fermentation is run in small volumes and then centralized.

In another non-limiting embodiment, the fermentation step and/or separation step is/may be carried out in a de-centralized facility with smaller fermenters present at location where substrate is available.

In yet another non-limiting embodiment, the separation step is/may be carried out in a larger centralized facility for downstream processing of the product to obtain the bio-based value added product.

In a non-limiting embodiment of the present disclosure, additional advantages provided by the processes (employing decentralized or centralized facility or a combination of both) enabling conversion of gaseous substrate to bio-based value added products include: easy and quick commissioning, reduced issues and loss from contamination, year-round output, consistent year round yield, better substrate availability, efficient waste management among other advantages as aforementioned. In order to overcome inherent problems with scale up and adapt to the local substrate availability, a horizontally scaled or decentralized go-to-market strategy would offer a sustainable solution. Smaller fermentation facilities can be set up closer to the points of waste generation. The product from smaller fermentation facilities can be separated from the fermentation milieu to a pre-form and brought stably to a centralized purification plant where it can be pooled and purified at scale. Since downstream processing is ~50-60% of the overall production cost, this allows for us to leverage the economies of scale for downstream processing while operating the fermentations as a decentralized network. This allows for unique commercialization solutions for waste management.

The present disclosure thus relates to a method for processing gaseous substrate(s) to obtain value added product(s), said method comprising:
fermenting the substrate(s) to obtain the product(s);
separating the product(s) obtained after fermentation; and
purifying the separated product(s)
wherein the fermentation is carried out by employing pre-determined/optimized parameter(s) of gas liquid mass transfer/or gas residence time, gas:air ratio, gas flow rate and air flow rate.

In a preferred embodiment, the gas liquid mass transfer or/gas residence time results from pore size of sparger in fermentor which is in the range of about 1 mm to about 2 nm, preferably in the range of about 1 um to about 2 nm; wherein the gas:air ratio is in the range of about 1:0.1 to about 1:5; and wherein the gas flow rate and the air flow rate is in the range of about 0.05 vvm to about 3 vvm.

In a preferred embodiment, the fermentation is carried out by employing gas velocity in the range of about 0.01 m/s to about 0.5 m/s, pressure in the range of about 0.5 bar to about 6 bar; temperature in the range of about 20° C. to about 50° C.; agitation in the range from about 200 rpm to about 1000 rpm; and pH in the range from about 3 to about 8.

In a preferred embodiment, the fermentation is carried out in a de-centralized facility, the separation is carried out in a de-centralized facility or centralized facility and wherein the purification is carried out in a centralized facility.

The present disclosure also relates to a method for facilitating processing of gaseous substrate(s) to value added product(s), said method comprising:
carrying out fermentation of the substrate(s) to obtain the product(s), at a de-centralized facility in proximity to the source of the substrate(s);

separating the product(s) obtained after fermentation at the said de-centralized facility or a centralized facility capable of purifying the separated product(s); and purifying the separated product(s), wherein the fermentation is carried out by employing pre-determined/optimized gas liquid mass transfer or/gas residence time, gas:air ratio, gas flow rate and air flow rate.

In a preferred embodiment, the gas liquid mass transfer/or gas residence time results from pore size of sparger in fermentor which is in the range of about 1 mm to about 2 nm, preferably in the range of about 1 um to about 2 nm; wherein the gas:air ratio is in the range of about 1:0.1 to about 1:5; and wherein the gas flow rate and the air flow rate is in the range of about 0.05 vvm to about 3 vvm.

The present disclosure herein below provides for certain examples for better understanding of the present disclosure. For purpose of illustration, examples below depict production of value added bio-based products such as lactic acid from gaseous substrates such as methane, wherein wild type methanotroph including but not limiting to M. capsulatus and recombinant M. capsulatus, are employed in the fermentation medium. However, a person skilled in the art would be aware that the examples provided herein are only prospective in nature and can be extrapolated to any type of value added products including but not limiting to organic acids with modifications which fall under the purview of the instant disclosure. Similarly, the fermentation, separation and purification steps as detailed by the Examples below, employ specific process parameters and optimal values for purpose of workability. However, said process parameters are not to be construed as limiting, and should be considered to encompass possibility of being workable in all the process parameter ranges and alternatives as detailed in the description herein.

Additional embodiments and features of the present disclosure will be apparent to one of ordinary skill in art based upon description provided herein. The embodiments herein provide various features and advantageous details thereof in the description. Descriptions of well-known/conventional methods and techniques are omitted so as to not unnecessarily obscure the embodiments herein. The examples provided herein are intended merely to facilitate an understanding of ways in which the embodiments herein may be practiced and to further enable those of skill in the art to practice the embodiments herein. Accordingly, the following examples should not be construed as limiting the scope of the embodiments herein.

EXAMPLES

The methanotrophic bacteria employed in the instant disclosure, has been deposited in accordance with the terms of the Budapest Treaty with the Microbial Type Culture Collection and Gene Bank (MTCC), Chandigarh, India:

| Identification ref. | Taxonomic designation | MTCC Accession number |
|---|---|---|
| STB31 | Methylococcus capsulatus | MTCC 25006 |
| STB18 | Methylococcus capsulatus | MTCC 25005 |

STB31 refers to the recombinant M. capsulatus strain capable of converting methane to lactic acid. STB18 refers to the recombinant M. capsulatus strain capable of converting methane to succinic acid. This deposit was made under the provisions of the Budapest Treaty on the International Recognition of the Deposit of Microorganisms for the Purposes of Patent Procedure and the Regulations thereunder (Budapest Treaty).

Materials and Methods:

Chemicals used in the examples are primarily obtained from Sigma Aldrich or HI Media. Enzymes are obtained from New England Biolabs. Membrane filters are obtained from Agilent technologies. Wildtype methanotroph strains are obtained from Prof. Colin Murrell's lab at the University of Norwich, UK.

Example 1

Growth by Fermentation of Wild Type Methanotrophs in an Optimized Reactor/Fermentor 1 ml DMSO stock of M. capsulatus is used to inoculate 20 ml of modified nitrate mineral salts medium taken in a 100 ml flask. The flask is sealed with suba seal and fed with methane upto 2.5 bar pressure. The culture is inoculated at 45° C. with 250 rpm agitation. When the OD reached 1, the cultures are used to inoculate 2*100 ml media taken in 2*500 ml flasks. The cultures are passaged in the 200 ml culture in conditions similar to above. Once the culture reaches an OD of 1, the culture is used to inoculate an optimized ALF reactor or STR containing 2.5 L media. The initial optical density of the medium is approximately 0.2 after the inoculation. Gas substrate required for the microorganism is constantly pumped into the reactor at at least 0.05 vvm flow rate or higher. pH of the media is controlled at 5.8. Temperature is controlled at 45° C. The exit gas from the reactor is recycled into specific points in the fermenter depending on the methane use. The influencing parameter such as pH, temperature, agitation, gas flow rate etc., are maintained until for 96 h. The growth is monitored by taking samples and measuring OD every 6-8 hrs. Methane and carbon dioxide in the exit gas are monitored using a Biogas analyzer.

Example 2

Figure 3:
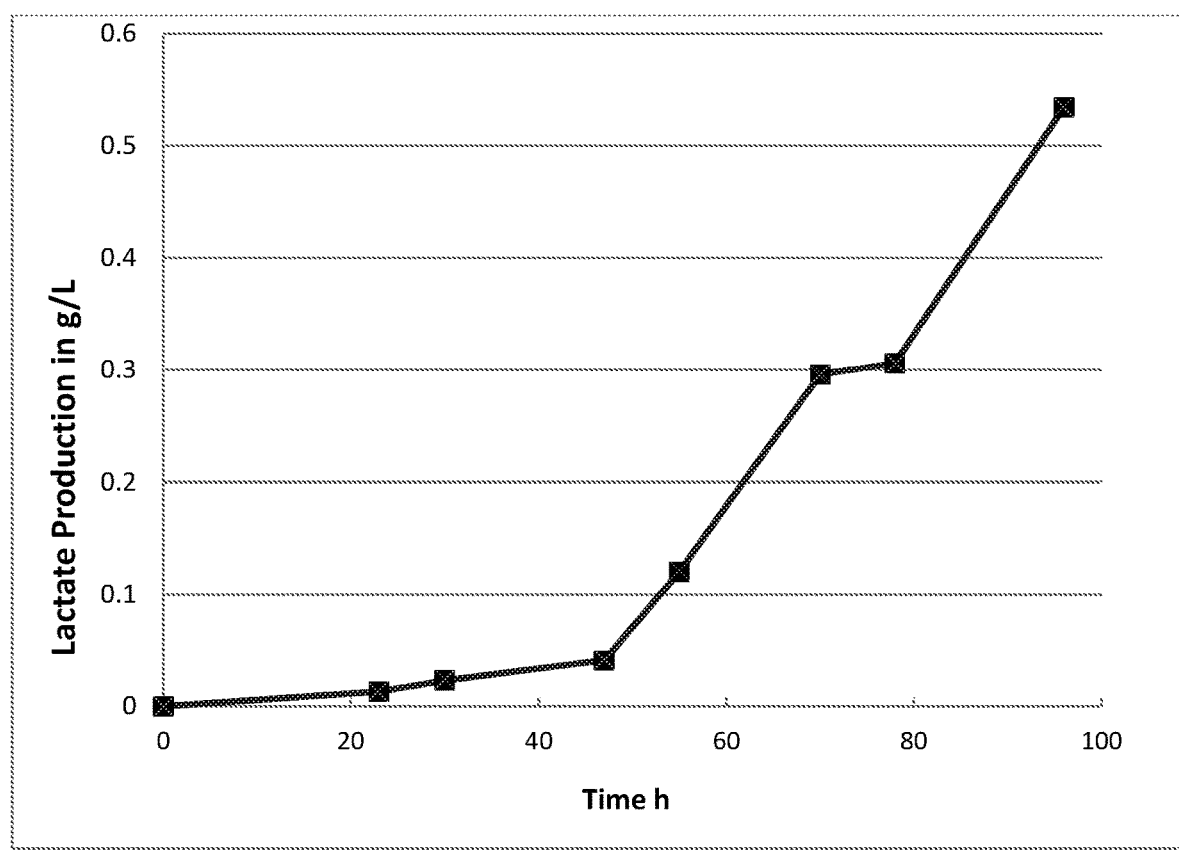
FIG. 3 illustrates lactic acid production from recombinant methanotroph strains over 96 hrs.

Growth by Fermentation of Recombinant Methanotrophs in Optimized Reactor/Fermentor for Organic Acid (Lactic Acid) Production M. capsulatus strain (STB31) that is specifically engineered for conversion of methane to lactic acid is used for fermentation of methane to lactic acid. 1 ml DMSO stock of recombinant M. capsulatus is used to inoculate 20 ml of modified nitrate mineral salts medium taken in a 100 ml flask. The flask is sealed with suba seal and fed with methane upto 2.5 bar pressure. The culture is inoculated at 45° C. with 250 rpm agitation. When the OD reached 1, the cultures are used to inoculate 2*100 ml media taken in 2*500 ml flasks. The cultures are passaged in the 200 ml culture in conditions similar to above. Once the culture reaches an OD of 1, the culture is used to inoculate an optimized ALF reactor or CSTR containing 2.5 L media. Gas substrate required for the microorganism is constantly pumped into the reactor at at least 0.05 vvm flow rate or higher. pH of the media is controlled at 5.8. Temperature is controlled at 45° C. The exit gas from the reactor is recycled into specific points in the fermenter depending on the methane use and lactic acid production. The influencing parameter such as pH, temperature, agitation, gas flow rate etc., are maintained throughout the process. The growth is monitored by taking samples and measuring OD every 6-8 hrs. Methane and carbon dioxide in the exit gas are monitored using a Biogas analyzer. Lactic acid present in the media is measured on HPLC using established methods. FIG. 3 depicts the lactic acid production from recombinant methanotroph strains over 96 hrs.

Separation of Lactic Acid

At the end of fermentation, the culture broth is passed through an ultra-filtration unit to remove the cells and other insoluble products. To the clear solution, required amount of calcium hydroxide is added and stirred constantly until the pH reaches 10.5 which simultaneously precipitates calcium lactate. The calcium lactate precipitate is filtered and re-dispersed in water to which 2N $H_2SO_4$ is added until the pH is reduced to 3 while precipitating calcium sulphate. The residue is filtered and a solution is obtained.

Purification of Lactic Acid

The filtered solution obtained post separation as per previous step is finally passed through a vacuum evaporator to concentrate the product to the desired level. The lactic acid is concentrated to about 50-80% in the evaporator.

Example 3

Growth by Fermentation of Recombinant Methanotrophs in Optimized Reactor/Fermentor for Organic Acid (Lactic Acid) Production

*M. capsulatus* (STB31) strain that is specifically engineered for conversion of methane to lactic acid is used for fermentation of methane to lactic acid. 1 ml DMSO stock of recombinant *M. capsulatus* is used to inoculate 20 ml of modified nitrate mineral salts medium taken in a 100 ml flask. The flask is sealed with suba seal and fed with methane upto 1.5 bar pressure. The culture is inoculated at 30° C. with 550 rpm agitation. When the OD reached 1, the cultures are used to inoculate 2*100 ml media taken in 2*500 ml flasks. The cultures are passaged in the 200 ml culture in conditions similar to above. Once the culture reaches an OD of 1, the culture is used to inoculate an optimized ALF reactor or STR containing 2.5 L media. Gas substrate required for the microorganism is constantly pumped into the reactor at at least 0.05 vvm flow rate or higher. pH of the media is controlled at 5.8. Temperature is controlled at 45° C. The exit gas from the reactor is recycled into specific points in the fermenter depending on the methane use and lactic acid production. The influencing parameter such as pH, temperature, agitation, gas flow rate etc., are maintained throughout the fermentation. The growth is monitored by taking samples and measuring OD every 6-8 hrs. Methane and carbon dioxide in the exit gas are monitored using a Biogas analyzer. Lactic acid present in the media is measured on HPLC using established methods.

Separation of Lactic Acid

At the end of fermentation, the culture broth is passed through an ultra-filtration unit to remove the cells and other insoluble products. To the clear solution, required amount of calcium hydroxide is added and stirred constantly until the pH reaches 10.5 which simultaneously precipitates calcium lactate. The calcium lactate precipitate is filtered and re-dispersed in water to which 2N $H_2SO_4$ is added until the pH is reduced to 3 while precipitating calcium sulphate. The residue is filtered and the solution is passed through a strong cation exchange resin, such as amberlite IR 120, to remove dissolved ion.

Purification of Lactic Acid

The solution obtained post exposure to filtration followed by adsorption by resin is finally passed through a vacuum evaporator to concentrate the product to the desired level. The product is concentrated to the desired technical grade level. The desired level can vary from 80% purity of lactic acid to >99% purity depending on the final application. For example, a purity of 85% is required for food grade. A purity of greater than 99% is required for polymer grade.

Example 4

Growth by Fermentation of Recombinant Methanotrophs in Optimized Reactor/Fermentor for Organic Acid (Lactic Acid) Production

*M. capsulatus* (STB31) strain that is specifically engineered for conversion of methane to lactic acid is used for fermentation of methane to lactic acid. 1 ml DMSO stock of recombinant *M. capsulatus* is used to inoculate 20 ml of modified nitrate mineral salts medium taken in a 100 ml flask. The flask is sealed with suba seal and fed with methane upto 5 bar pressure. The culture is inoculated at 50° C. with 500 rpm agitation. When the OD reached 1, the cultures are used to inoculate 2*100 ml media taken in 2*500 ml flasks. The cultures are passaged in the 200 ml culture in conditions similar to above. Once the culture reaches an OD of 1, the culture is used to inoculate an optimized ALF reactor or STR containing 2.5 L media. Gas substrate required for the microorganism is constantly pumped into the reactor at at least 0.05 vvm flow rate or higher. pH of the media is controlled at 5.8. Temperature is controlled at 45° C. The exit gas from the reactor is recycled into specific points in the fermenter depending on the methane use and lactic acid production. The influencing parameter such as pH, temperature, agitation, gas flow rate etc., are maintained throughout the fermentation time. The growth is monitored by taking samples and measuring OD every 6-8 hrs. Methane and carbon dioxide in the exit gas are monitored using a Biogas analyzer. Lactic acid present in the media is measured on HPLC using established methods.

Separation of Lactic Acid

At the end of fermentation, the culture broth is passed through an ultra-filtration unit to remove the cells and other insoluble products. The clear solution obtained from ultra-filtration is passed through an ion exchange resin, such as amine based resins, which has a very high affinity towards organic acids. The product acid is adsorbed, thus separated.

Purification of Lactic Acid

The adsorbed product acid is taken to the centralized facility (FIG. 1) for further purification, where primarily the product is eluted using a strong base such as NaOH, later passed through an ion exchange resin and later concentrated using an evaporator.

Example 5

Growth by Fermentation of Recombinant Methanotrophs in Optimized Reactor/Fermentor for Organic Acid (Succinic Acid) Production

*M. capsulatus* strain (STB18) that is specifically engineered for conversion of methane to succinic acid is used for fermentation of methane to succinic acid. 1 ml DMSO stock of recombinant *M. capsulatus* is used to inoculate 20 ml of modified nitrate mineral salts medium taken in a 100 ml flask. The flask is sealed with suba seal and fed with methane upto 0.5 bar pressure. The culture is inoculated at 20° C. with 200 rpm agitation. When the OD reached 1, the cultures are used to inoculate 2*100 ml media taken in 2*500 ml flasks. The cultures are passaged in the 200 ml culture in conditions similar to above. Once the culture reaches an OD of 1, the culture is used to inoculate an optimized ALF reactor or STR containing 2.5 L media. Gas substrate required for the microorganism is constantly pumped into the reactor at at least 0.05 vvm flow rate or higher. pH of the media is controlled at 3. Temperature is controlled at 20° C. The exit gas from the reactor is recycled into specific points in the fermenter depending on the methane use and succinic acid production. The influencing parameter such as pH, temperature, agitation, gas flow rate etc., are maintained throughout the process. The growth is monitored by taking samples and measuring OD every 6-8 hrs. Methane and carbon dioxide in the exit gas are monitored using a Biogas analyzer. Succinic acid present in the media is measured on HPLC using established methods.

Separation of Succinic Acid

At the end of fermentation, the culture broth is passed through an ultra-filtration unit to remove the cells and other insoluble products. To the clear solution, required amount of calcium hydroxide is added and stirred constantly until the pH reaches 10.5 which simultaneously precipitates calcium succinate. The calcium succinate precipitate is filtered and re-dispersed in water to which 2N $H_2SO_4$ is added until the pH is reduced to 3 while precipitating calcium sulphate. The residue is filtered and a solution is obtained.

Purification of Succinic Acid

The filtered solution obtained post separation as per previous step is finally passed through a vacuum evaporator to concentrate the product to the desired level. The succinic acid is concentrated to about 50-80% in the evaporator.

Example 6

Growth by Fermentation of Recombinant Methanotrophs in Optimized Reactor/Fermentor for Organic Acid (Succinic Acid) Production M. capsulatus strain that is specifically engineered for conversion of methane to succinic acid is used for fermentation of methane to succinic acid. 1 ml DMSO stock of recombinant M. capsulatus is used to inoculate 20 ml of modified nitrate mineral salts medium taken in a 100 ml flask. The flask is sealed with suba seal and fed with methane upto 2.5 bar pressure. The culture is inoculated at 45° C. with 250 rpm agitation. When the OD reached 1, the cultures are used to inoculate 2*100 ml media taken in 2*500 ml flasks. The cultures are passaged in the 200 ml culture in conditions similar to above. Once the culture reaches an OD of 1, the culture is used to inoculate an optimized ALF reactor or STR containing 2.5 L media. Gas substrate required for the microorganism is constantly pumped into the reactor at at least 0.05 vvm flow rate or higher. pH of the media is controlled at 5.8. Temperature is controlled at 45° C. The exit gas from the reactor is recycled into specific points in the fermenter depending on the methane use and succinic acid production. The influencing parameter such as pH, temperature, agitation, gas flow rate etc., are maintained throughout the fermentation. The growth is monitored by taking samples and measuring OD every 6-8 hrs. Methane and carbon dioxide in the exit gas are monitored using a Biogas analyzer. Succinic acid present in the media is measured on HPLC using established methods.

Separation of Succinic Acid

At the end of fermentation, the culture broth is passed through an ultra-filtration unit to remove the cells and other insoluble products. To the clear solution, required amount of calcium hydroxide is added and stirred constantly until the pH reaches 10.5 which simultaneously precipitates calcium succinate. The calcium succinate precipitate is filtered and re-dispersed in water to which 2N $H_2SO_4$ is added until the pH is reduced to 3 while precipitating calcium sulphate. The residue is filtered and the solution is passed through a strong cation exchange resin, such as amberlite IR 120, to remove dissolved ion.

Purification of Succinic Acid

The solution obtained post exposure to filtration followed by adsorption by resin is finally passed through a vacuum evaporator to concentrate the product to the desired level. The product is concentrated to the desired technical grade level. The desired level can vary from 80% purity of lactic acid to >99% purity depending on the final application. For example, a purity of 85% is required for food grade. A purity of greater than 99% is required for polymer grade.

Example 7

Growth by Fermentation of Recombinant Methanotrophs in Optimized Reactor/Fermentor for Organic Acid (Succinic Acid) Production M. capsulatus strain (STB18) that is specifically engineered for conversion of methane to succinic acid is used for fermentation of methane to succinic acid. 1 ml DMSO stock of recombinant M. capsulatus is used to inoculate 20 ml of modified nitrate mineral salts medium taken in a 100 ml flask. The flask is sealed with suba seal and fed with methane upto 5 bar pressure. The culture is inoculated at 50° C. with 500 rpm agitation. When the OD reached 1, the cultures are used to inoculate 2*100 ml media taken in 2*500 ml flasks. The cultures are passaged in the 200 ml culture in conditions similar to above. Once the culture reaches an OD of 1, the culture is used to inoculate an optimized ALF reactor or STR containing 2.5 L media. Gas substrate required for the microorganism is constantly pumped into the reactor at at least 0.05 vvm flow rate or higher. pH of the media is controlled at 5.8. Temperature is controlled at 45° C. The exit gas from the reactor is recycled into specific points in the fermenter depending on the methane use and succinic acid production. The influencing parameter such as pH, temperature, agitation, gas flow rate etc., are maintained throughout the fermentation time. The growth is monitored by taking samples and measuring OD every 6-8 hrs. Methane and carbon dioxide in the exit gas are monitored using a Biogas analyzer. Succinic acid present in the media is measured on HPLC using established methods.

Separation of Succinic Acid

At the end of fermentation, the culture broth is passed through an ultra-filtration unit to remove the cells and other insoluble products. The clear solution obtained from ultra-filtration is passed through an ion exchange resin, such as amine based resins, which has a very high affinity towards organic acids. The product acid is adsorbed, thus separated.

Purification of Succinic Acid

The adsorbed product acid is taken to the centralized facility for further purification, where primarily the product is eluted using a strong base such as NaOH, later passed through an ion exchange resin and later concentrated using an evaporator.

Example 8

Decentralized Facility for Production of Lactic Acid/Succinic Acid from Waste

Figure 2:
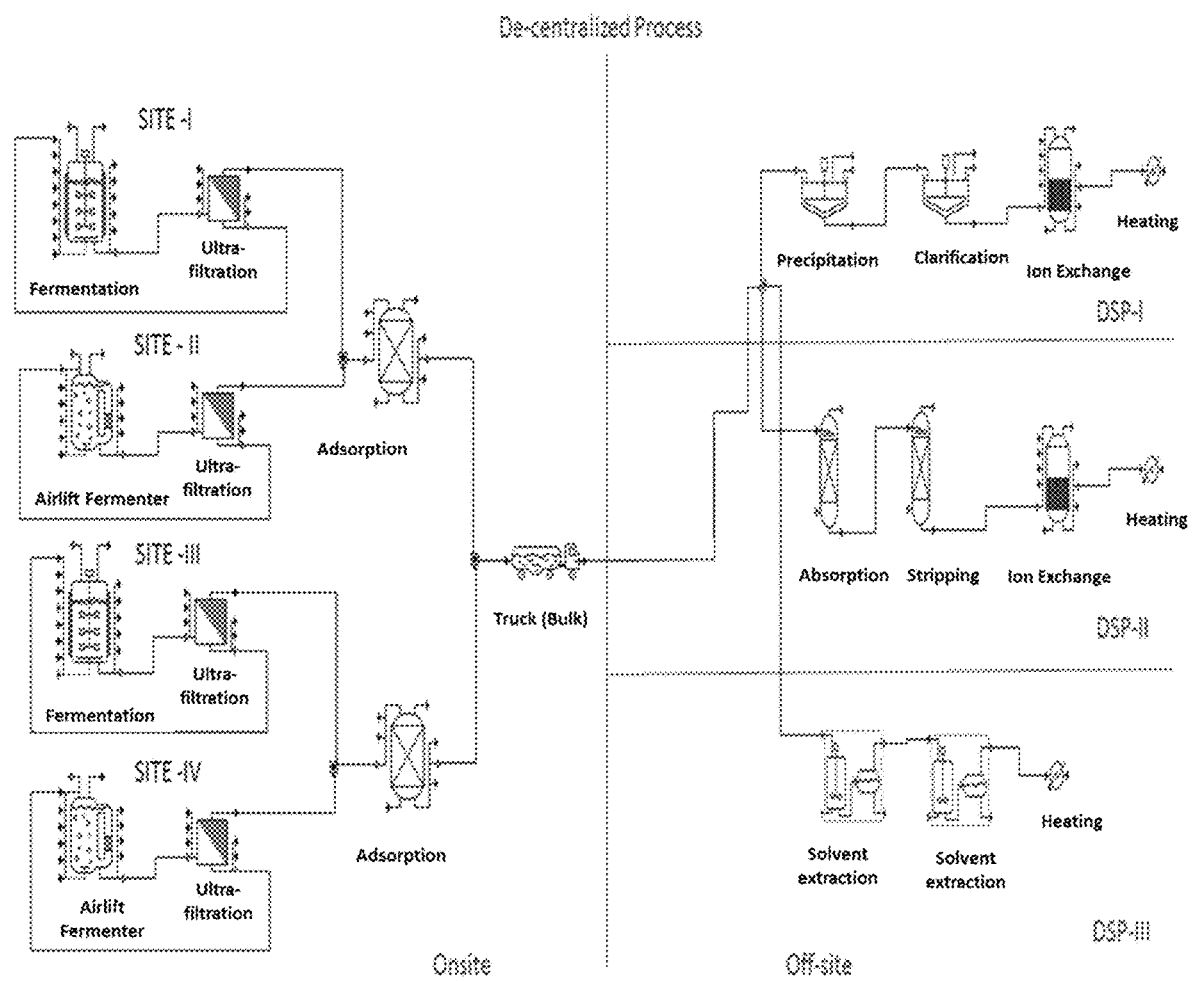

Lactic acid/Succinic acid production from waste using a decentralized process (FIG.-2) happens in two distinct steps. Step 1 involves the fermentation of methane/biogas to products in multiple small sized STR or ALF fermentors at different location where the gaseous substrate is produced. These facilities are anywhere from 5000 L to a 100,000 L capacity reactor. This reduces the cost of transportation of the gas and other raw materials. The separation of lactic acid/succinic acid from fermentation broth is achieved by precipitating lactic acid/succinic acid as calcium lactate or calcium succinate using calcium hydroxide/calcium carbonate or adsorption of lactic acid/succinic acid onto weak anion exchange resin such as amber lite IRA 96 or IR 67 which has high affinity for organics. The calcium lactate/succinate or the resin as solid is transported to the centralized purification facility where further purification is done. Step 2 involves a centralized division for processing the separated crude and further purification of the product by solvent extraction, reverse osmosis, evaporation, distillation, electro dialysis and/or bipolar electro dialysis. Different grades of lactic acid/succinic acid thus can be manufactured by different purification processes. Depending on the market needs, different grades of lactic acid/succinic are made.

Example 9

Growth by Fermentation of Recombinant Methanotrophs in Optimized Reactor/Fermentor for Organic Acid (Lactic Acid) Production.

Said example involves optimization of gas residence time/gas liquid mass transfer. *M. capsulatus* is grown using methane in a 5 L STR to optimize the gas residence time. The inoculum from shake flask is used to pitch 3 L of modified mineral salts medium in a 5 L reactor. Methane and air mixture is fed into the medium using a sparger with pore size of 1 mm at at least 0.3 vvm flow rate or higher. pH of the media is controlled at 5.8. Temperature is controlled at 45° C. The influencing parameter such as pH, temperature, agitation, gas flow rate etc., are maintained throughout the growth period. The growth is monitored by taking samples and measuring OD every 6-8 hrs. Methane and carbon dioxide in the exit gas are monitored using a Biogas analyzer.

The fermentation is repeated first with a sparger with a pore size of 22 micron and then with 500 nm pore size. As the pore size decreases, the size of the gas bubble generated in the liquid phase decreases. This in turn increases the gas residence time and enhances overall productivity (Table 1, below). The productivity is increased by almost 3× when the sparger pore size is reduced from mm to microns and almost to 10×, when the sparger pore size is reduced to nm. Obtained product is further subjected to separation and purification as per aforementioned examples.

used to pitch 3 L of modified mineral salts medium in a 5 L reactor. Methane and air mixture is fed into the medium using a sparger with pore size of 1 mm at at least 0.05 vvm flow rate or higher. pH of the media is controlled at 5.8. Temperature is controlled at 45° C. The influencing parameter such as pH, temperature, agitation, gas flow rate etc., are maintained until the fermentation time. The growth is monitored by taking samples and measuring OD every 6-8 hrs. Methane and carbon dioxide in the exit gas are monitored using a Biogas analyzer.

The fermentation is repeated with the reactor pressurized to 1, 2, 3 or 4 bar pressure. As the pressure increases (>1 bar), solubility of methane in the liquid phase increases. This in turn enhances overall productivity. Growth of the strains were also not affected upto 5 bar pressure. Obtained product is further subjected to separation and purification as per aforementioned examples.

Example 11

The gas flow rate can significantly affect the productivity of the gaseous fermentation. *M. capsulatus* is grown using methane in a 5 L STR. The inoculum from shake flask is used to pitch 3 L of modified mineral salts medium in a 5 L reactor. Methane and air mixture is fed into the medium using a sparger with pore size of 20 um. pH of the media is controlled at 5.8. Temperature is controlled at 45° C. The influencing parameter such as pH, temperature, agitation etc., are maintained until the fermentation time. The growth is monitored by taking samples and measuring OD every 6-8 hrs. Methane and carbon dioxide in the exit gas are monitored using a Biogas analyzer.

The fermentation is started with a flow rate of 0.024 vvm of methane and 0.2 vvm of air. The methane to air ratio is maintained at 1:10. The methanotroph strains grow to a maximum OD with a productivity of 0.03 g/L/H of dry cell weight. The fermentation is repeated keeping the methane to air ratio the same and varying the flow rate of methane and air. As the methane and air flow rates were varied, the productivity of the biomass production increases from 0.03 g/L/H to almost 0.1 g/L/H. Below table 2 summarizes the variation in biomass productivity with varying methane and air flow rates.

TABLE 1

| Pore size | Dia, (micron) | Radius, (micron) | Area, mm$^2$ | Vol, ml | Area/Vol | Ratio | Improvement in productivity of methane conversion |
|---|---|---|---|---|---|---|---|
| 1 mm | 1000 | 500 | 3.14 | 0.5233 | 6 | 1 | 1 |
| 22 micron | 22 | 11 | 0.0015 | 5.572E-06 | 272.72 | 45.45 | 3 |
| 500 nm | 0.5 | 0.25 | 7.85E-07 | 6.542E-11 | 12000 | 2000 | 10 |
|  |  |  | $4\pi r^2$ | $4/3\pi r^3$ |  |  |  |

Example 10

Growth by Fermentation of Wildtype Methanotrophs in Optimized Reactor/Fermentor.

Said example provides optimization of gas pressure to enable enhanced solubility of methane in liquid medium.

Increasing pressure significantly enhances solubility of methane in the liquid phase. *M. capsulatus* is grown using methane in a 5 L STR. The inoculum from shake flask is

TABLE 2

| CH4 flow (vvm) | Air Flow (vvm) | Productivity (g/l/hr) |
|---|---|---|
| 0.02 | 0.2 | 0.0323 |
| 0.06 | 0.48 | 0.0654 |

TABLE 2-continued

| CH4 flow (vvm) | Air Flow (vvm) | Productivity (g/l/hr) |
|---|---|---|
| 0.72 | 0.6 | 0.1 |
| 0.08 | 0.6 | 0.0971 |

Example 12

The methane to air ratio can significantly affect the productivity of the gaseous fermentation. *M. capsulatus* is grown using methane in a 5 L STR. The inoculum from shake flask is used to pitch 3 L of modified mineral salts medium in a 5 L reactor. Methane and air mixture is fed into the medium using a sparger with pore size of 22 um. pH of the media is controlled at 5.8. Temperature is controlled at 45° C. The influencing parameter such as pH, temperature, agitation etc., are maintained until the fermentation time. The growth is monitored by taking samples and measuring OD every 6-8 hrs. Methane and carbon dioxide in the exit gas are monitored using a Biogas analyzer.

The fermentation is started with a flow rate of 0.04 vvm of methane and 0.04 vvm of air. The methane to air ratio is maintained at 1. The methanotroph strains grow to a maximum OD with a productivity of 0.1 g/L/H of dry cell weight. The fermentation is repeated varying the methane to air ratio at 0.1, 0.2, 0.3 and 0.5. As the methane and air ratio is varied, the productivity of the biomass production increased from 3 fold to almost 24 fold.

Example 13

Continuous Production of Biomass from Methane *M. capsulatus* is grown using methane in a 5 L STR. The inoculum from shake flask is used to pitch 3 L of modified mineral salts medium in a 5 L reactor. Methane and air mixture is fed into the medium using a sparger with pore size of 22 micron. pH of the media is controlled at 5.8. Temperature is controlled at 45° C. The influencing parameter such as pH, temperature, agitation, etc., are maintained throughout the fermentation. After 48 h, once the OD reaches 5, the fermentation is switched over time to a continuous process. The dilution rate of the modified nitrate mineral salts medium is varied from 0.05 to 0.3 h−1. For each change in dilution rate the fermentation is allowed to stabilize for 3-4 reactor volumes. At each dilution rate, growth is monitored by taking samples and measuring OD every 6-8 hrs. Methane and carbon dioxide in the exit gas are monitored using a Biogas analyzer.

Figure 4:
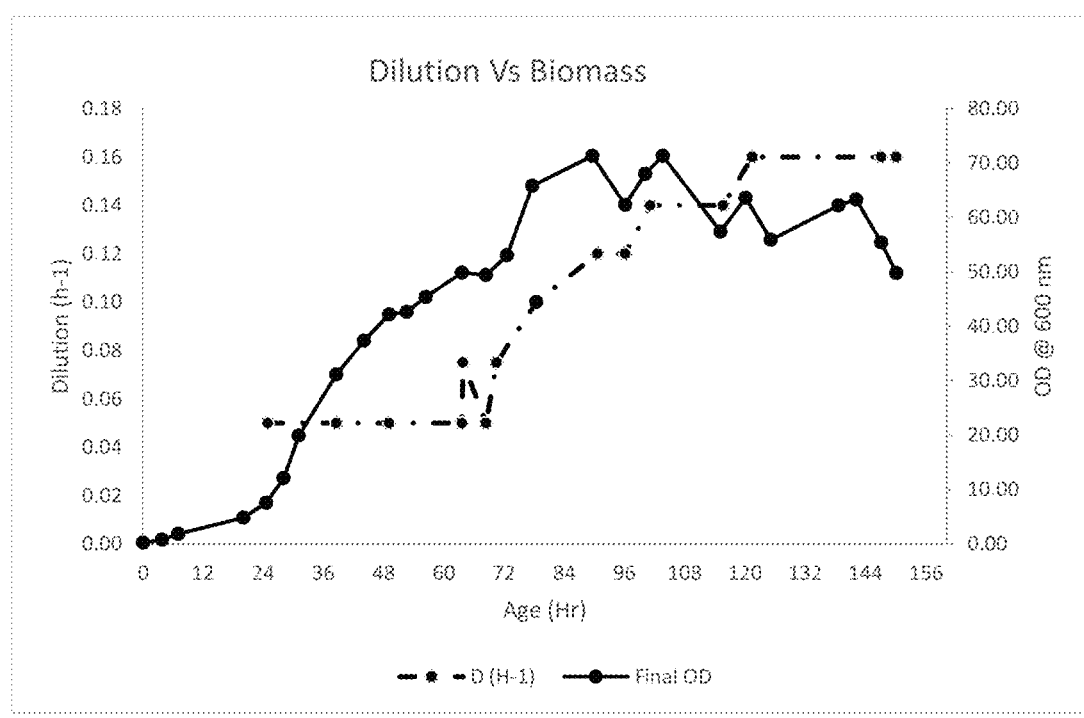
FIG. 4 illustrates growth of wild type *M. capsulatus* in methane and biogas.

Once the culture stabilizes at a specific dilution rate of 0.2 h−1, the process is maintained stably for extended period of time. FIG. 4 depicts the continuous increase in dilution rate and OD of the culture over an extended period of time. This allows the extraction of specific amounts of product from the fermentations set up every 24 hrs, thus enabling to have a year round output.

Example 14

Growth by Fermentation of Methanotrophs in Optimized Reactor/Fermentor for Biomass Production, with Substrate being Methane and Biogas Biogas is mostly a mixture of methane and carbon dioxide with other minor impurities. The percentage of methane in the biogas usually varies from 40-60%. The remaining being largely carbon dioxide.

Biogas used for this analysis is from an anaerobic digester that processes kitchen waste. The composition of the biogas is (55-65% methane; 45-35% CO2). For methane, a commercial mixture of 95% CH4:5% CO2 is used.

Figure 5:
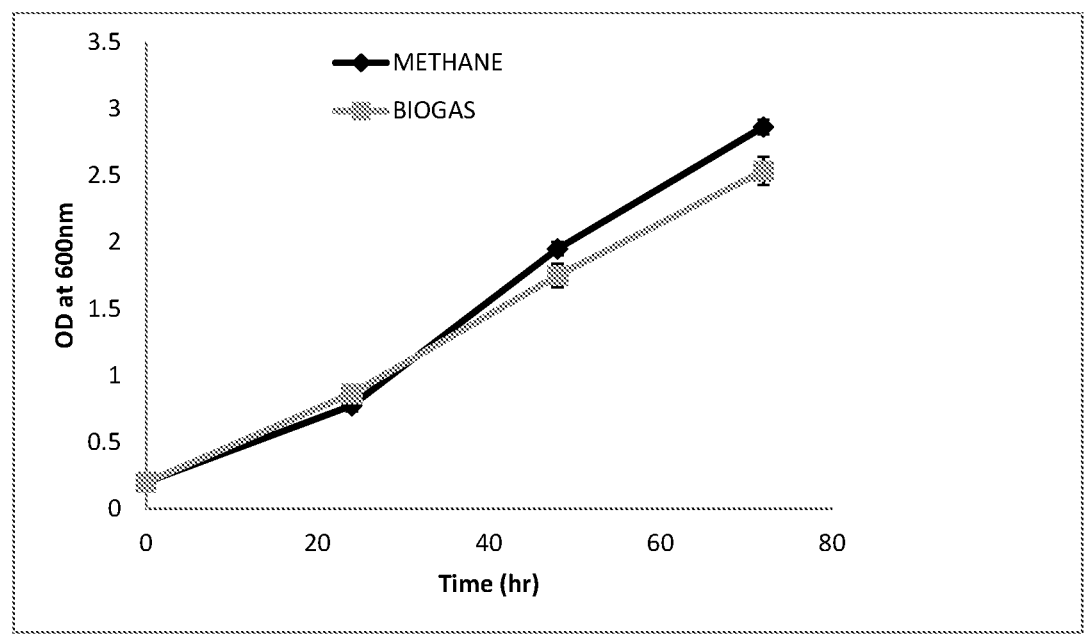
FIG. 5 illustrates continuous production of biomass from methane in a STR.

*M. capsulatus* is grown using methane in a 5 L STR. The inoculum from shake flask is used to pitch 3 L of modified mineral salts medium in a 5 L reactor. Methane or biogas is mixed with air and fed into the medium using a sparger with pore size of 1 mm at at least 0.2 vvm flow rate or higher. pH of the media is controlled at 5.8. Temperature is controlled at 45° C. The influencing parameter such as pH, temperature, agitation, gas flow rate etc., are maintained until for 96 h. The growth is monitored by taking samples and measuring OD every 6-8 hrs. Methane and carbon dioxide in the exit gas are monitored using a Biogas analyzer. FIG. 5 shows the comparative growth profiles on methane and biogas. The growth is comparable with varying ratios of methane and carbon dioxide. Gas obtained by fermentation is thereafter separated and purified as per examples aforementioned.

The biomass produced in Examples 6-12 is processed to SCP (single cell protein).

The concentrated biomass separated from the fermentation media is converted into a dry and stable product. While many methods are available, for ease of operation and economic reasons, cell treatment is carried out by heat treatment followed by dehydration through drying. For this, the biomass is treated at 140° C. for 10-20 seconds. This process lyses the cells and simultaneously degrades the nucleic acid concentration. To obtain the dry product, wet cells are air dried at 60° C. The cells are dried by a spray, drum or fluidized bed dryer.

The present disclosure in view of the above described illustrations and various embodiments, is thus able to successfully overcome the various deficiencies of prior art and provide for an improved method for production of value added products from gaseous substrates.

We claim:

1. A method for processing gaseous substrate(s) selected from methane, biogas or a combination thereof to obtain value added product(s), said method comprising:
    fermenting the substrate(s) to obtain the product(s);
    separating the product(s) obtained after fermentation; and
    purifying the separated product(s),
    wherein the fermentation is carried out by employing parameter of a gas liquid mass transfer or gas residence time resulting from pore size of sparger in a fermenter which is in the range of about 2 nm to about 1 mm, a gas:air ratio in the range of about 1:0.1 to about 1:5, and, a gas flow rate and an air flow rate in the range of about 0.05 vvm to about 3 vvm.

2. The method as claimed in claim 1, wherein the parameter are optimized such that the gas conversion rate is at least 1 g/L/h.

3. The method as claimed in claim 1, wherein the value added product is organic acid(s), single cell protein or carotenoid(s).

4. The method as claimed in claim 3, wherein the organic acid is selected from a group consisting of lactic acid, succinic acid, formic acid, acetic acid and malic acid; and wherein the carotenoid is selected from a group consisting of beta-carotene, lutein, zeaxanthin, lycopene, astaxanthin, annatto or any combination thereof.

5. The method as claimed in claim 1, wherein the fermentation is carried out in presence of methanotrophic bacteria or bacteria selected from a group consisting of *Methylococcus capsulatus, Methylobacterium extorquens, Methylomicrobium album, Methylocapsa acidiphila, Meth-*

*ylobacterium organophilum, Methylobacterium mesophilicum, Methylobacterium dichloromethanicum, Methylocella silvestris, Methylosinus trichosporium, Methylobacillus flagellatus KT, Methylibium petroleiphilum PM1, Methylobacterium nodulans, Methylobacterium populi, Methylobacterium chloromethanicum, Methylacidiphilum infernorum V4, Methylophilus methylotrophus, Methylomonas methanica, Methylobacterium rhodesianum MB 126, Methylobacter tundripaludum, Methylobacterium sp. 4-46, Methylovorus glucosetrophus SIP3-4, Mycobacterium smegmatis, Methylobacterium rhodesianum, Methylosinus sporium, Methylocella palustris, Methylobacterium fujisawaense, Methylocystis parvus, Methylovulum miyakonense, Methylobacterium rhodinum, Methylocystis echinoides, Methylomonas rubra, Methylococcus thermophilus, Methylobacterium aminovorans, Methylobacterium thiocyanatum, Methylobacterium zatmanii, Acidithiobacillus ferrivorans, Methylobacterium aquaticum, Methylobacterium suomiense, Methylobacterium adhaesivum, Methylobacterium podarium, Methylobacter whittenburyi, Crenothrix polyspora, Clonothrix fusca, Methylobacter bovis, Methylomonas aurantiaca, Methylomonas fodinarum, Methylobacterium variabile, Methylocystis minimus, Methylobacter vinelandii, Methylobacterium hispanicum, Methylomicrobium japanense, Methylococcaceae bacterium,* and *Methylocystis methanolicus.*

6. The method as claimed in claim 5, wherein the bacteria is *Methylococcus capsulatus, Methylosinus trichosporium, Methylocella silvestris, Methylobacterium extorquens.*

7. The method as claimed in claim 1, wherein the fermentation is carried out in continuous, batch or semi-continuous mode, in a reactor/fermenter selected from a group consisting of stirred tank reactor (STR) and air lift fermentor (ALF); wherein said culturing is carried out in presence of culture media comprising organic and inorganic source of nitrogen optionally along with trace elements.

8. The method as claimed in claim 1, wherein the gas liquid mass transfer or gas residence time results from pore size of sparger in fermenter which is in the range of about 1 um to about 2 nm.

9. The method as claimed in claim 1, wherein the fermentation is carried out by employing gas velocity in the range of about 0.01 m/s to about 0.5 m/s, pressure in the range of about 0.5 bar to about 6 bar; temperature in the range of about 20° C. to about 50° C.; agitation in the range from about 200 rpm to about 1000 rpm; and pH in the range from about 3 to about 8.

10. The method as claimed in claim 1, wherein the separation is carried out by one or more techniques selected from a group consisting of filtration, precipitation, adsorption, membrane separation, centrifugation or any combination of techniques thereof.

11. The method as claimed in claim 1, wherein the purification is carried out by techniques selected from a group consisting of electro-dialysis, solvent extraction, reactive extraction, reverse osmosis, filtration, precipitation, membrane separation, chromatographic separation, drying, distillation, ion-exchange and evaporation or any combination of techniques thereof.

12. The method as claimed in claim 1, wherein the fermentation is carried out in a de-centralized facility, the separation is carried out in a de-centralized facility or centralized facility and the purification is carried out in a centralized facility.

13. A method for facilitating processing of gaseous substrate(s) to value added product(s), said method comprising:
   carrying out fermentation of the substrate(s) to obtain the product(s), at a de-centralized facility in proximity to the source of the substrate(s);
   separating the product(s) obtained after fermentation at the said de-centralized facility or a centralized facility capable of purifying the separated product(s); and
   purifying the separated product(s),
   wherein the fermentation is carried out by employing a gas liquid mass transfer or gas residence time resulting from pore size of sparger in a fermenter which is in the range of about 2 nm to about 1 mm, a gas:air ratio in the range of about 1:0.1 to about 1:5, and, a gas flow rate and an air flow rate in the range of about 0.05 vvm to about 3 vvm.

14. The method as claimed in claim 13, wherein the gas liquid mass transfer or gas residence time results from pore size of sparger in fermenter which is in the range of about 1 um to about 2 nm.

* * * * *